United States Patent [19]

Fremery et al.

[11] 4,400,557
[45] Aug. 23, 1983

[54] PROCESS FOR THE O-SUBSTITUTION OF PHENOLS

[75] Inventors: Max Fremery, Wesseling; Joachim Korff, Bornheim-Sechtem, both of Fed. Rep. of Germany

[73] Assignee: Braunkohlen Kraftstoff Aktiengesellschaft, Wesseling, Fed. Rep. of Germany

[21] Appl. No.: 263,770

[22] Filed: May 14, 1981

[30] Foreign Application Priority Data

Feb. 4, 1981 [DE] Fed. Rep. of Germany ....... 3103665

[51] Int. Cl.$^3$ ............................................. C07C 37/16
[52] U.S. Cl. ..................................... 568/804; 568/794
[58] Field of Search ................................ 568/804, 794

[56] References Cited

U.S. PATENT DOCUMENTS 2,448,942 9/1948 Winkler et al. ...................... 568/804
3,855,318 12/1974 Nakajima et al. ................... 568/804
4,329,517 5/1982 Taniguchi et al. .................. 568/804

FOREIGN PATENT DOCUMENTS 2127083 12/1971 Fed. Rep. of Germany ...... 568/804
7512390 4/1976 Netherlands ........................ 568/804

*Primary Examiner*—Werren B. Lone
*Attorney, Agent, or Firm*—Connolly and Hutz

[57] ABSTRACT

This invention relates to a process for reacting phenol, mono- and di-alkyl phenols having at least one free o-position with methanol and/or dimethyl ether in the gas phase to form o-substituted phenols in the presence of a catalyst of oxides of iron, vanadium, at least one oxide of boron, aluminum, titanium, zirconium, silicon, germanium, tin and lead, and at least one oxide of an alkali metal, alkaline-earth metal, lanthanum and manganese.

6 Claims, No Drawings

PROCESS FOR THE O-SUBSTITUTION OF PHENOLS

BACKGROUND OF THE INVENTION (1) Field of the Invention

This invention relates to a process for reacting phenol, mono- and di-alkyl phenols having at least one free o-position with methanol and/or dimethyl ether in the gas phase to form o-substituted phenols in the presence of a catalyst of oxides of iron, vanadium, at least one oxide of boron, aluminum, titanium, zirconium, silicon, germanium, tin and lead, and at least one oxide of an alkali metal, alkaline-earth metal, lanthanum and manganese.

(2) Description of the Prior Art

The production of o-substituted phenols, for example o-cresol and 2,6-dimethyl phenol is of considerable commercial interest. Although various synthesis processes are known from the patent literature, there has never been a process by which o-substitution products can be obtained highly selectively from phenols having free o-positions with production times that are long enough for practical application.

Although phenol can be reacted to form 2,6-dimethyl phenol with a selectivity of the order of 99% in accordance with German Offenlegungsschrift No. 21 27 083, a selectivity of only 95% is obtained where o-cresol is used as the starting material.

German Offenlegungsschrift No. 19 48 607 describes a process in which o-cresol is converted into 2,6-dimethyl phenol with a selectivity of around 84%. Conversely, a selectivity of 98% is obtained with o-cresol as the starting product according to German Offenlegungsschrift No. 24 28 056. Where phenol is used, however, a selectivity of only 96,5% is achieved, falling to 92% after 150 hours.

SUMMARY OF THE INVENTION

According to the present invention, it has been found that phenols having at least one free o-position can be substituted in the o-positions by catalytic reaction with alcohols and/or their ethers by reacting phenol and/or mono- and/or di-alkyl phenols with methanol and/or dimethyl ether in a molar ratio of 1:0.1–10 at a temperature of between 270° to 390° C. for 0,05 to 10 seconds in the gas phase in the presence of a catalyst consisting of oxides of iron, vanadium, at least one oxide of boron, aluminum, titanium, zirconium, silicon, germanium, tin and lead and of at least one oxide of an alkali metal, alkaline-earth metal, lanthanum and manganese.

DESCRIPTION OF THE PREFERRED EMBODIMENTS

For alkylating phenol, mono- or di-alkyl phenols with methanol and/or dimethyl ether, the starting material or mixtures thereof are vaporised in the usual way and introduced in the ratio indicated below into a reactor in which the catalyst is arranged, for example in the form of a fixed bed. The reaction may also be carried out with advantage in a fluidised bed. In addition, steam may be introduced with the starting products in such a quantity that the molar ratio of phenol and/or alkyl and di-alkyl phenol to steam amounts to about 1:1–5. The reactor is operated at a temperature in the range from 270° to 390° C. and preferably at a temperature in the range of from 300° C. to 380° C. The reaction is generally carried out at normal pressure, although it may also be carried out with advantage under elevated pressure, for example up to around 30 bars.

The catalysts may be produced in known manner. From the oxides of the elements of the 3. und 4. group of the Periodic System the oxides of boron, aluminum, germanium, titanium and silicon are preferred.

Furthermore, the oxides of barium, calcium, strontium and manganese are preferred.

The starting materials are used in such a quantity that a residence time of 0.05 to 10 seconds and preferably from 0,1 to 5 seconds is obtained.

After leaving the reactor, excess alcohol or ether is removed by distillation from the product mixture. The product mixture is then separated from the aqueous phase. Unreacted starting materials are distilled off and returned to the reactor.

By using the catalyst containing vanadium oxide, the selectivity with which substitution takes place in the free o-positions generally amounts to 98% or more. Even after a production time of 2000 hours, there are still no signs of any significant reduction in the selectivity of the catalyst. A major advatange of the process according to the invention lies in the fact that the consumption of methanol is considerably lower than in conventional processes, particularly by working with a fluidised catalyst bed or under elevated pressure.

The process according to the invention is illustrated by the following Examples:

EXAMPLE 1

A mixture of o-cresol and phenol, methanol and water in a molar ratio of 1 (o-cresol and phenol) to 4.2 (methanol) to 2.6 (water) was introduced in vapour form into a fixed-bed reactor heated to about 360° C. and containing a catalyst consisting of iron oxide, vanadium oxide, titanium oxide and barium oxide in a molar ratio of 100:10:2:1. The starting materials were introduced under normal pressure in a quantity such that the residence time amounted to 3 seconds. The product leaving the reactor was cooled in countercurrent to the starting materials.

Excess methanol was distilled off from the condensate accumulating. The aqueous phase was separated off from the sump. The small quantity of o-cresol and phenol was distilled off from the organic phase, of which 98,7% consisted of o-cresol and 2.6-xylenol, and returned to the reactor. The 2.6-xylenol remaining in the sump, which still contained 0.8% of 2.4.6-trimethyl phenol, was subjected to fine distillation in another column. The total yield of 2.6-xylenol, based on o-cresol and phenol, amounted to 99%. The 2,6-xylenol obtained overhead was 99.9% pure.

EXAMPLE 2

Phenol, methanol and water in a molar ratio of 1:5:2.5 were reacted in the vapour phase in the same way as described in Example 1. After working up, 2.6-xylenol was obtained with a selectivity of 99%.

The experiment was repeated with a molar ratio of 1:0.8:2 at a reaction temperature of 340° C.

O-cresol was obtained with a selectivity of 93% and 2.6-xylenol with a selectivity of 6.5%.

EXAMPLE 3 o-Cresol, methanol and water in a ratio of 1:2.5:2.5 were reacted in the same way as described in Example 1. The catalyst contained iron oxide, vanadium oxide, titanium oxide and calcium oxide in a molar ratio of 100:22:2:1.5. After working up, 2.6-xylenol was obtained with a selectivity of 98%.

EXAMPLE 4 m-Cresol, methanol and water in a molar ratio of 1:5:2.5 were reacted in the same way as described in Example 1. The catalyst contained iron oxide, vanadium oxide, boron oxide and barium oxide in a molar ratio of 100:15:2:1.

After working up, 2.3.6-trimethyl phenol was obtained with a selectivity of 99.2%.

EXAMPLE 5 p-Cresol and methanol in a molar ratio of 1:5 were reacted in the same way as described in Example 1, except that the pressure was 6 bars. The catalyst contained iron oxide, vanadium oxide, aluminum oxide and potassium oxide in a molar ratio of 100:10:2:1,5.

After working up, 2.4.6-trimethyl phenol was obtained with a selectivity of 94%.

EXAMPLE 6

Phenol, dimethyl ether and water in a ratio of 1:2:2.6 were reacted in the same way as described in Example 1 in a fixed bad reactor. The catalyst contained iron oxide, vanadium oxide, titanium oxide and barium oxide in a ratio of 100:10:2:1.

After working up, 2.6-xylenol was obtained with a selectivity of 99%.

After repeating the experiment, but with a catalyst containing tin oxide instead of titanium oxide, the selectivity obtained was 91.9%.

EXAMPLE 7

A mixture of o-cresol and phenol, dimethyl ether and water in a molar ratio of 1:2:2.6 was reacted in vapour phase as described in Example 1 in a fixed bed reactor.

The catalyst consisted of iron oxide, vanadium oxide, silicon oxide and manganese oxide in a molar ratio of 100:10:2:0.1.

After working up, 2.6-xylenol was obtained with a selectivity of 99%.

EXAMPLE 8

A mixture of o-cresol and phenol, dimethyl ether and water in a molar ratio of 1:2:2.6 were reacted as described in Example 1. The catalyst contained iron oxide, vanadium oxide, silicon oxide and barium oxide in a molar ratio of 100:2:10:0.1. After working up, 2.6-xylenol was obtained with a selectivity of 99%.

EXAMPLE 9 o-Cresol, methanol and water in a ratio of 1:2,5:2,5 were reacted in the same way as described in Example 1.

The catalyst contained iron oxide, vanadium oxide, silicon oxide and barium oxide in a molar ratio of 100:150:10:1,5.

After working up, 2.6-xylenol was obtained with a selectivity of 99.2%.

What is claimed is:

1. In a process for the production of o-substituted phenols by catalytically reacting phenols having at least one free o-position with alcohols or ethers in the presence of a catalyst containing iron oxide at an elevated temperature in the gaseous phase, the improvement which comprises reacting a compound selected from the group consisting of phenol, mono-alkyl phenol, and di-alkyl phenol with methanol or dimethyl ether in a molar ratio of 1:0.1–10 at a temperature of between 270° C.–390° C. for 0.05 to 10 seconds in the gaseous phase in the presence of a four component catalyst consisting essentially of (a) iron oxide, (b) vanadium oxide, (c) at least one oxide of a metal of the group consisting of boron, aluminum, titanium, zirconium, silicon, germanium, tin and lead, and (d) at least one oxide of a metal of the group consisting of an alkali metal, an alkaline-earth metal, lanthanum and manganese when component (c) is an oxide of silicon or when component (c) is an oxide other than silicon, component (d) is at least one oxide of a metal of the group consisting of calcium, strontium, barium, an alkali metal and lanthanum.

2. A process as claimed in claim 1, wherein the reaction is carried out at a temperature in the range from 300° C. to 380° C.

3. A process as claimed in claim 1, wherein the residence time is from 0.1 to 5 seconds.

4. A process as claimed in claim 1, wherein the catalyst contains an oxide of germanium, titanium, zirconium or silicon.

5. A process as claimed in claim 1, wherein the catalyst contains an alkaline-earth oxide or manganese oxide.

6. A process as claimed in claim 1, wherein the molar ratio between the oxidic components amounts to 100:1–200:0.1–30:0.01–10.

* * * * *